United States Patent

Dixon et al.

[11] 3,955,958
[45] May 11, 1976

[54] α-CYANO-α-DIALKYLPHOSPHONATO ACETANILDE HERBICIDES

[75] Inventors: William D. Dixon, Kirkwood, Mo.; Maureen E. Becker, Glen Ellyn, Ill.

[73] Assignee: Monsanto Company, St. Louis, Mo.

[22] Filed: Mar. 3, 1975

[21] Appl. No.: 554,869

Related U.S. Application Data

[62] Division of Ser. No. 495,958, Aug. 9, 1974, Pat. No. 3,907,937.

[52] U.S. Cl. ........................................ 71/87; 71/86
[51] Int. Cl.$^2$ ............................................ A01N 9/36
[58] Field of Search .................................. 71/87, 86

[56] References Cited
UNITED STATES PATENTS 3,005,010  10/1961  Grisley .............................. 71/86 X
3,764,676  10/1973  Kerst et al. ........................ 71/86 X

*Primary Examiner*—Lewis Gotts
*Assistant Examiner*—Catherine L. Mills
*Attorney, Agent, or Firm*—William I. Andress; Donald W. Peterson

[57] ABSTRACT

α-cyano-α-dialkylphosphonato acetanilides are prepared by reacting an α-cyano-α-dialkylphosphonate carbanion with an aromatic isocyanate or isothiocyanate. The said carbanion may be generated in situ by the reaction of an alkali metal or reactive compound thereof with an α-cyano-α-dialkylphosphonato acetanilide.

Compounds within the scope of the invention described herein are pesticidally active, e.g., as herbicides.

7 Claims, No Drawings

α-CYANO-α-DIALKYLPHOSPHONATO ACETANILDE HERBICIDES

This is a division of application Ser. No. 495,958, filed Aug. 9, 1974, now U.S. Pat. No. 3,907,937.

BACKGROUND OF THE INVENTION

1. Field of the Invention

The invention herein pertains to the field of acetanilide compounds, their manufacture and their use as herbicides. In more particular, the invention pertains to the field of α-cyano-α-dialkylphosphonato acetanilides and their use as active ingredients in herbicidal compositions. The compounds herein are prepared by the reaction of an α-cyano-α-dialkylphosphonate carbanion with aromatic isocyanates or isothiocyanates.

2. Description of the Prior Art

In the prior art are found various pesticidal, e.g., insecticidal or herbicidal compositions whose active ingredients are composed of compounds having various nitrogen/phosphorus/oxygen and/or sulfur-derived configurations, produced by a variety of methods. For example, in U.S. Pat. No. 3,057,774 are described insecticidal carbamoylalkyl phosphonothioate compositions prepared by the reaction of an ammonium or alkali metal salt of phosphonothioic acid with halohydrocarbylamide in an anhydrous medium.

A further example of prior art compounds as described above is found in U.S. Pat. No. 3,776,984 which discloses as pre-emergent herbicidal compounds S-dichloromethyl oxyphosphorus thioates prepared from substituted dichloromethane sulfenyl chlorides by reaction with a tertiary oxyphosphorus compound. Among various groups which may be substituted on the dichloromethane sulfenyl moiety are those having the —CONR$_2$ structure wherein the R's may be, e.g., hydrogen, phenyl or substituted phenyl.

Numerous other examples may be found in the prior art of pesticidal compounds having other nitrogen/phosphorus/oxygen and/or sulfur configurations. However, to applicants' knowledge, the compounds and process for preparing them as described herein are novel.

SUMMARY OF THE INVENTION

In one embodiment the present invention pertains to a novel class of α-cyano-α-dialkylphosphonato acetanilide compounds. The compounds according to this invention have the following generic structural formula:

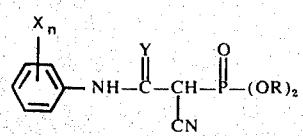

wherein X represents a hydrogen, halogen, CN or $C_{1-10}$ alkyl or alkoxy, both preferably having from 1–5 carbon atoms; $n$ is an integer from 0–5, preferably from 0–2; Y is oxygen or sulfur and each R is an alkyl group which may be the same or different and having from 1–10 carbon atoms, and preferably a lower alkyl group having from 1–5 carbon atoms.

In another embodiment of the invention herbicidal compositions are provided comprising said novel α-cyano-α-dialkylphosphonato acetanilides as the active ingredient and an adjuvant.

Still another embodiment of the invention consists of a novel process which comprises the reaction of an α-cyano-α-dialkylphosphonate carbanion with an aromatic isocyanate or isothiocyanate. Suitably, said carbanion is generated in situ from the α-cyano-α-dialkylphosphonate by use of an alkali metal or reactive compound, e.g., a hydride, alkyl or alkoxide thereof.

DESCRIPTION OF PREFERRED EMBODIMENTS

The process according to the present invention is believed to proceed according to the following typical reaction sequence:

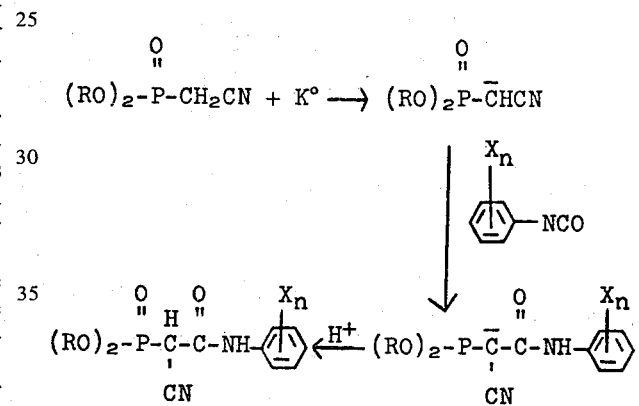

Analogous compounds wherein Y in the above generic formula is sulfur are produced when an isothiocyanate is substituted for the isocyanate in the above reaction sequence.

The invention will be more clearly understood by reference to the following detailed description of specific embodiments thereof.

EXAMPLE 1

This example describes the preparation of α-cyano-α-diethylphosphonato-4-methylacetanilide. A solution of diethyl cyanomethylphosphonate, 8.9 g. (0.05 mol), and potassium t-butoxide, 6.9 g. (0.062 mol) in 150 ml dry tetrahydrofuran was stirred for 1 hour. To the reaction was added slowly a solution of p-tolylisocyanate, 7.3 g. (0.055 mol), in 40 ml dry tetrahydrofuran; cooling was applied to maintain the temperature at 20°. After the addition of materials, the reaction was stirred overnite, neutralized with 5.3 g. of conc. hydrochloric acid. The reaction mixture was condensed, then extracted with methylene chloride. Extracts were combined, dried and condensed. The residue was recrystallized twice from isopropanol, 8.9 g. (57%); mp. 160°–165°.

Anal. Calc'd for $C_{14}H_{19}N_2O_4P$: C, 54.19; H, 6.17. Found: C, 53.98; H, 6.11.

EXAMPLE 2

In this example is described the preparation of α-cyano-α-(diethylphosphonato)-3-chloroacetanilide.

Diethyl cyanomethylphosphonate, 8.9 g. (0.05 mol) and m-chlorophenylisocyanate, 8.4 g. (0.55 mol) placed in 75 ml of dry tetrahydrofuran and a solution of potassium t-butoxide, 6.9 g. (0.062 mol) in 75 ml of tetrahydrofuran added over one hour with cooling to maintain the temperature at 10°–15°C. After the addition the reaction was stirred at room temperature for 3 days, neutralized with hydrochloric acid and the solvent removed in vacuuo. Residue treated with 75 ml water and extracted twice with 100 ml methylene chloride. Extracts were combined, dried and evaporated to give 16.3 g of a yellow solid which was recrystallized twice from isopropanol, mp 143°–148°C.

Anal. Calc'd for $C_{13}H_{16}ClN_2O_4P$: C, 47.21; H, 4.88. Found: C, 47.07; H, 4.85.

EXAMPLE 3

This example describes the preparation of α-cyano-α-(diethylphosphonato)-2-methoxyacetanilide.

A solution of diethyl α-cyanomethylphosphonate, 8.9 g. (0.05 mol) and o-methoxyphenylisocyanate, 8.2 g. (0.055 mol) in 75 ml of dry tetrahydrofuran was treated with stirring and cooling with a solution of 6.9 g. (0.062 mol) potassium t-butoxide in 75 ml of dry tetrahydrofuran. After the addition was complete, the reaction stirred for 4 hours, neutralized with hydrochloric acid and condensed. Residue treated with 75 ml of water and extracted twice with 100 ml of methylene chloride. The extracts were combined, dried, and evaporated to give 13 g. of a yellow solid which was recrystallized from isopropanol; mp 106°–110°C.

Anal. Calc'd for $C_{14}H_{19}N_2O_5P$: C, 51.53; H, 5.87. Found: C, 51.74; H, 5.90.

EXAMPLE 4

In this example, an aromatic isothiocyanate is used in place of an isocyanate to produce the corresponding thio compound.

Diethyl α-cyanomethylphosphonate, 8.9 g. (0.05 mol), was added slowly at 35°C to a well stirred suspension of potassium metal in 200 ml of toluene. After the addition was complete, the reaction stirred for 2 hours and then phenyl isothiocyanate, 6.7 g. (0.05 mol) added dropwise. The reaction stirred for 90 minutes and then with 10 ml of isopropanol to destroy any unreacted potassium. The reaction acidified with 3 g. acetic acid. After addition of 15 ml of water, the organic layer was separated, dried and condensed to a solid which recrystallized from isopropanol, mp 125°–130°C. The product was identified as α-cyano-α-diethylphosphonatothioacetanilide.

Anal. Calc'd for $C_{13}H_{16}N_2O_3PS$: C, 50.15; H, 5.18. Found: C, 49.86; H, 5.41.

EXAMPLE 5

This example describes the preparation of another thio compound, α-cyano-α-diethylphosphonato-p-cyanothioacetanilide.

A suspension of potassium t-butoxide, 6.9 g. (0.06 mol) in 100 ml of toluene was added slowly to a solution of diethyl cyanomethylphosphonate, 8.9 g. (0.5 mol) and p-cyanophenyl isothiocyanate, 8.0 g. (0.05 mol) in 150 ml of toluene. The reaction was stirred overnite, neutralized with 3.6 g. glacial acetic acid. After addition of 70 ml of water, the organic layer separated. The water layer was extracted 3 times with 75 ml of methylene dichloride. The extracts and the original organic layer were combined, dried and condensed to a gummy residue which was recrystallized from isopropanol and then benzene as a yellow solid; mp 123°–127°C.

EXAMPLE 6

In this example is described the preparation of α-cyano-α-(diethylphosphonato) acetanilide.

Sodium hydride, 2.6 g. (50% oil dispersion) was placed in 200 ml of dry tetrahydrofuran and diethyl α-cyanomethylphosphonate, 8.8 g. (0.05 mol) added slowly over a 30 minute period. The reaction was stirred for 1 hour and then phenylisocyanate, 6.0 g. (0.05 mol) added slowly. The reaction was stirred for 3 hours, neutralized with 5 g. of hydrochloric acid and then the solvent removed in vacuuo. The residue was treated with 50 ml of water and filtered. The solid dried and recrystallized from isopropanol 9.6 g.; mp 161°–164°C.

Anal. Calc'd for $C_{13}H_{17}N_2O_4P$: C, 52.70; H, 5.79. Found: C, 52.68; H, 5.59.

EXAMPLE 7

This example describes the preparation of α-cyano-α-(diethylphosphonato)-3,4-dichloroacetanilide.

Sodium hydride, 2.6 g. (50% oil dispersion) placed in 200 ml dry tetrahydrofuran and diethyl α-cyanomethylphosphonate, 8.8 g. (0.05 mol) added slowly over 30 minutes. The reaction was stirred for one hour and then 3,4-dichlorophenylisocyanate, 9.5 g. (0.05 mol) in 100 ml tetrahydrofuran added. The reaction was stirred for 3 hours, neutralized with 5 g. hydrochloric acid and the solvent removed in vacuuo. The residue was treated with 75 ml of water and filtered. The solid was recrystallized twice from isopropanol, 9.0 g.; mp 178°–182°C.

Anal. Calc'd for $C_{13}H_{15}Cl_2N_2O_4P$: C, 42.45; H, 4.14. Found: C, 42.45; H, 3.99.

EXAMPLE 8

This example describes the preparation of α-cyano-α-(diethylphosphonato)-4-chloroacetanilide.

Sodium hydride, 2.6 g. (50% oil dispersion), placed in 150 ml of dry tetrahydrofuran and diethyl α-cyanomethylphosphonate, 8.8 g. (0.05 mol), added slowly over 20 minutes. The reaction was stirred for 40 minutes and then p-chlorophenylisocyanate, 7.7 g. (0.05 mol) in 50 ml tetrahydrofuran was added slowly. The reaction allowed to stand overnite, acidified with 5.3 g. hydrochloric acid and the solvent removed in vacuuo. The residue was treated with 75 ml water and extracted twice with 50 ml methylene dichloride. The extracts were combined, dried and evaporated to 16 g. of a yellow solid which was recrystallized twice from ethanol; mp 144°–152°C.

Anal. Calc'd for $C_{13}H_{16}ClN_2O_4P$: C, 47.21; H, 4.88. Found: C, 47.51; H, 5.03.

The process variations according to the present invention have no critical parameters for the operation thereof. That is, temperatures and concentrations of reactants, time of reaction, etc., are straightforward and will be selected by those skilled in the art to accomplish the intended result within the scope of the exemplified invention having reference to the particular materials used and products produced. Thus, the α-cyano-α-dialkylphosphonate, alkali metal or reactive compound thereof and aromatic isocyanate or isothiocyanate may be reacted in such concentrations at such temperatures and times as effects formation of the invention compounds described herein. Temperatures suitable for reaction of the α-cyano-α-dialkylphosphonate with the alkali metal or reactive compound thereof to produce the corresponding phosphonate carbanion may be within the range of from about 20°C to about 110°C; preferred operating temperature ranges are from about 30°C to about 70°C. Reaction of the isocyanate or isothiocyanate reactant with said phosphonate carbanion may be performed using equimolar quantities, although more or less of either may be used, at temperatures within a range of from about 10°C to 100°C, preferably from about 20°C to about 50°C.

Further modifications within the process of this invention, as indicated above, include the use of reactive compounds of the alkali metals, such as the hydrides, alkoxides and alkyls of lithium, sodium, potassium, rubidium and cesium to generate the phosphonate carbanion. The alkoxide and alkyl moieties in these compounds may have generally from 1–10 carbon atoms and preferably from 1–5 carbon atoms. Obviously, other inert carriers, diluents or solvents may be used in which to conduct the above-exemplified reactions. For example, aliphatic and cycloaliphatic hydrocarbons such as the alkanes, alkenes, cycloalkanes and cycloalkenes customarily used for such purposes. Also suitable are aromatic hydrocarbons, such as the xylenes, etc., halogenated hydrocarbons such as the halobenzenes, etc. Heterocyclic compounds, e.g., tetrahydrofuran, etc., may also be used as a reaction medium herein.

Additional compounds produced according to the process of this invention include those wherein, referring to the generic formula above, X is a chloro, bromo, iodo or fluoro radical which may be substituted in from 0–5 positions on the anilide ring. Also, the R's in the above formula may be the same or different of any $C_{1-10}$ alkyl group, preferably a $C_{1-5}$ alkyl group, which may be straight or branched-chain.

Compounds according to this invention have been found to be herbicidally active when applied preemergently and/or postemergently, as typified by the examples below.

EXAMPLE 9

Contact herbicidal activity of representative α-cyano-α-dialkylphosphonato acetanilides of this invention is determined by the following procedure:

The compound to be tested is applied in spray form to plants of a given age of several grasses and broadleaf species. After the plants are the desired age, each aluminum pan of plants is sprayed with a given volume of a 0.2% concentration solution of the candidate chemical, corresponding to a rate of approximately 4 lbs. per acre. This solution is prepared from an aliquot of a 2% solution of the candidate compound in acetone, a known amount of cyclohexanone-emulsifying agent mix, and sufficient water to make up to volume. The emulsifying agent is a mixture comprising 35 wt. percent butylamine dodecylbenzene sulfonate and 65 wt. percent of a tall oil ethylene oxide condensate having about 6 moles of ethylene oxide per mole of tall oil. The injuries to the plants are then observed approximately 14 days later and the results are recorded.

Contact herbicidal activity of the compounds prepared in Examples 2 and 3 is observed against Canada thistle. Contact herbicidal activity of the compound prepared in Example 3 is also observed against morningglory and cocklebur. Contact herbicidal activity of the compound prepared in Example 4 is observed against lambsquarters and for the compound of Example 5 contact herbicidal activity is observed against quackgrass and downy brome.

EXAMPLE 10

Pre-emergent herbicidal activity of representative α-cyano-α-dialkylphosphonato acetanilides of this invention is determined by the following procedure:

A good grade of top soil is placed in aluminum pans and compacted to a depth of ⅜ to ½ inch from the top of the pan. A pre-determined number of seeds of each of several plant species are placed on top of the soil in the pans. The seeds are covered with soil and the pans leveled. The herbicidal composition is applied by spraying the surface of the top layer of soil with a solution containing a sufficient amount of active ingredient to obtain a rate of application of 5 lbs. per acre. The pans are then placed on a sand bench in the greenhouse and watered from below as needed. The plants are observed at the end of approximately 14 days and the results recorded.

Pre-emergent herbicidal activity of the compound prepared in Example 1 is observed against nutsedge. Pre-emergent activity of the compounds prepared in Examples 2 and 4 is observed against Johnsongrass. Pre-emergent activity of the compound prepared in Example 4 is also observed against lambsquarters and downy brome.

The herbicidal compositions of this invention including concentrates which require dilution prior to application contain an effective amount of at least one active ingredient and an adjuvant in liquid or solid form. The compositions are prepared by admixing the active ingredient with an adjuvant including diluents, extenders, carriers and conditioning agents to provide compositions in the form of finely-divided particulate solids, granules, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these.

The compositions of this invention can also contain other additaments, e.g., fertilizers, herbicides, other pesticides and the like used as adjuvants or in combination with the above-described adjuvants.

While the illustrative embodiments of the invention have been described hereinbefore with particularity, it will be understood that various other modifications will be apparent to and can readily be made by those skilled in the art without departing from the scope and spirit of the invention. Accordingly, it is not intended that the scope of the claims appended hereto be limited to the examples and description set forth herein but rather the claims be construed as encompassing all the features of patentable novelty which reside in the present invention including all features which would be treated as equivalents thereof by those skilled in the art to which the invention pertains.

What is claimed is:

1. Herbicidal compositions comprising an adjuvant and an effective amount of a compound having the formula

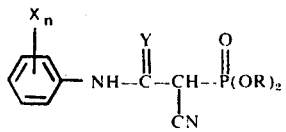

wherein:
X is halogen, CN, or a $C_{1-10}$ alkyl or alkoxy group;
$n$ is an integer from 0–5;
Y is oxygen or sulfur and the
R's are alkyl groups having from 1–10 carbon atoms.

2. Composition according to claim 1 wherein in said formula $n$ is zero.

3. Composition according to claim 1 wherein in said formula X is CN, $n$ is 1 and each R is ethyl.

4. Composition according to claim 3 wherein in said formula Y is sulfur.

5. Composition according to claim 1 wherein in said formula X is lower alkyl, $n$ is 1 and each R is ethyl.

6. Composition according to claim 1 wherein in said formula X is halogen, $n$ is 1 and each R is ethyl.

7. Composition according to claim 1 wherein in said formula X is a lower alkoxy group, $n$ is 1 and both R's are ethyl.

* * * * *